(12) United States Patent
Bodor

(10) Patent No.: US 8,835,410 B2
(45) Date of Patent: Sep. 16, 2014

(54) TREATMENT OF EYELID DERMATITIS

(75) Inventor: Nicholas S. Bodor, Bal Harbour, FL (US)

(73) Assignee: Bodor Laboratories, Inc., Miami, FL (US)

( * ) Notice: Subject to any disclaimer, the term of this patent is extended or adjusted under 35 U.S.C. 154(b) by 71 days.

(21) Appl. No.: 13/104,846

(22) Filed: May 10, 2011

(65) Prior Publication Data

US 2012/0289486 A1    Nov. 15, 2012

(51) Int. Cl.
*A61K 31/56*    (2006.01)
*A61K 31/573*    (2006.01)

(52) U.S. Cl.
CPC ............... *A61K 31/56* (2013.01); *A61K 31/573* (2013.01); *Y10S 514/914* (2013.01)
USPC ......................................... 514/170; 514/914

(58) Field of Classification Search
USPC ......................................... 514/169, 171, 912
See application file for complete search history.

(56) References Cited

U.S. PATENT DOCUMENTS

| 3,828,080 | A | 8/1974 | Phillips et al. |
| 4,285,937 | A | 8/1981 | Kalvoda |
| 4,996,335 | A | 2/1991 | Bodor |
| 7,560,448 | B2 | 7/2009 | Bodor |
| 7,687,484 | B2 | 3/2010 | Bodor |
| 7,923,441 | B2 * | 4/2011 | Bodor ........................... 514/171 |
| 2005/0026892 | A1 * | 2/2005 | Bodor ........................... 514/179 |
| 2005/0182039 | A1 | 8/2005 | Meyering |
| 2005/0222110 | A1 | 10/2005 | Bartels |
| 2007/0110812 | A1 | 5/2007 | Xia et al. |

FOREIGN PATENT DOCUMENTS

GB    1384372    2/1975

OTHER PUBLICATIONS

Bramble, How to Treat Contact Dermatitis Around the Eye Area, www.eHow.com, Mar. 24, 2010, printed from http://web.archive.org/web/20100324014559/http://www.ehow.com/how_5675597_treat-dermatitis-around-eye-area.html, 3 pages.*

Kelchner, Symptoms of Contact Dermatitis on Eyelids, Sep. 28, 2009, www.eHow.com, pritned from http://www.ehow.com/print/about_5437861_symptoms-contact-dermatitis-eyelids.html, Google date sheet of entry included,3 pages.*

\* cited by examiner

*Primary Examiner* — Gigi Huang
(74) *Attorney, Agent, or Firm* — Dentons US LLP

(57) ABSTRACT

A method for the treatment of eyelid dermatitis and/or dermatitis of the periorbital area is provided.

16 Claims, No Drawings

TREATMENT OF EYELID DERMATITIS

BACKGROUND

1. Field of the Invention

The invention relates to a method of treating eyelid dermatitis.

2. Background Art

Eyelid dermatitis is characterized by eyelid skin which is inflamed, scaly, weeping, erythematous and/or pruritic; often this condition extends to other parts of the periorbital area, particularly under the eye. While the causes of this condition are various, including psoriasis, seborrhea, rosacea, contact urticaria, atopic dermatitis and contact dermatitis, treatment of eyelid dermatitis can be problematic because the eyelid and other periorbital skin is naturally thin and moist. Eyelid skin is, moreover, occluded because it retracts when the lid is open. Anti-inflammatory corticosteroids are generally known to cause skin atrophy, making their use especially contraindicated in thin-skinned areas.

Topical or other local application of potent glucocorticoids can produce severe toxic effects such as Cushingoid features, pituitary-adrenal suppression, skin atrophy, immunosuppression, weight gain and inhibition of wound healing. Other kinds of toxic responses, including allergies and cataracts, have resulted from long term use of drugs of this type.

Ophthalmic application of glucocorticosteroids presents additional problems. The protective mechanisms built into the eye allow only small amounts of doses applied to the eye to reach the target sites within the eye; generally, over 90 percent of the total dose will find its way into the general circulation. This in turn leads to serious systemic side effects of the type described above. Moreover, there is a more serious and specific side effect when these drugs are used in the eye, which is an increase in intraocular pressure (IOP). Corticosteroid-induced chronic or acute glaucoma has in fact been reported since the early 1960's. Generally, the corticosteroid is needed only topically to control the inflammation. However, the absorbed steroid is responsible for the serious side effects noted above. It is believed that the effect of the corticosteroid on the aqueous outflow pathway and adjacent tissue glycosaminoglycans (GAG's) is important in the development of glucocorticoid-induced ocular hypertension. Because of their tendency to elevate ocular pressure and to cause cataracts, the FDA has generally forbidden use of topical anti-inflammatory corticosteroids on the eyelid or periorbital skin and even facial skin in general.

The natural glucocorticosteroids and many of their marketed derivatives are $\Delta^4$ and $\Delta^{1,4}$ pregnenes having 21-hydroxy substituents. There are, however, a number of anti-inflammatory $\Delta^4$ and $\Delta^{1,4}$ androstenes described in the literature; note, for example, British Patent Specification No. 1,384,372; Phillipps et al. U.S. Pat. No. 3,828,080 and Kalvoda et al. U.S. Pat. No. 4,285,937.

In recent years, soft steroids have been developed in an effort to provide compounds having potent anti-inflammatory activity with minimal systemic activity. One series of soft steroids which is described as having potent anti-inflammatory activity with minimal systemic activity consists of the 17α-carbonates of Bodor U.S. Pat. No. 4,996,335. These compounds include as preferred embodiments haloalkyl 17α-alkoxycarbonyloxy-11β-hydroxyandrost-4-en-3-one-17β-carboxylates and the corresponding $\Delta^{1,4}$ compounds, optionally bearing 6α- and/or 9α-fluorine and 16α- or 16β-methyl substituents. One of these compounds is chloromethyl 17α-ethoxycarbonyloxy-11β-hydroxyandrosta-1,4-dien-3-one-17β-carboxylate, also known as loteprednol etabonate.

Loteprednol etabonate is presently marketed in the United States by Bausch & Lomb Pharmaceuticals, Inc. as Alrex® and Lotemax® and combined with tobramycin as Zylet® for ophthalmic use. Other uses of loteprednol etabonate are currently or have been in clinical trials (for rhinitis and various dermatological conditions).

Loteprednol etabonate has an impressive safety profile for its FDA-approved ophthalmic uses. It has now been marketed in the US for thirteen years, with approximately three million prescriptions written, for a variety of FDA-approved ophthalmic indications, including allergic conjunctivitis, general inflammatory conjunctivitis, post cataract surgery inflammation and uveitis.

SUMMARY

In one aspect, there is provided herein a method for the treatment of eyelid dermatitis and/or dermatitis of the periorbital area, which comprises applying to the eyelid and/or periorbital area, respectively, of a subject in need of such treatment, an anti-inflammatory effective amount of a dermatological composition comprising loteprednol etabonate and a dermatologically acceptable carrier therefor. Loteprednol etabonate (LE) is also known by its chemical name, chloromethyl 17α-ethoxycarbonyloxy-11β-hydroxyandrosta-1,4-dien-3-one-17β-carboxylate.

In a second aspect, said method utilizes an anti-inflammatory effective amount of a dermatological composition which comprises loteprednol etabonate and a compound having the formula:

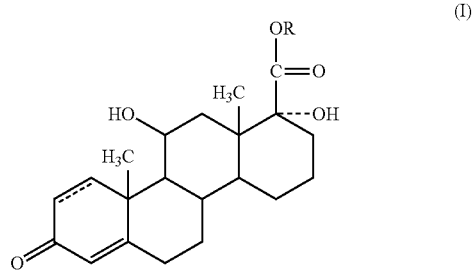

(I)

wherein R is H or $CH_3$ and the dotted line in ring A indicates that the 1,2-linkage is saturated or unsaturated, the amount of the compound of formula (I) being sufficient to enhance the anti-inflammatory activity or duration of action, or both, of loteprednol etabonate, and a dermatologically acceptable carrier therefor.

In a third aspect, said method utilizes an anti-inflammatory effective amount of a dermatological composition which comprises loteprednol etabonate and a compound selected from the group consisting of hydrocortisone (cortisol), corticosterone and 11-deoxycortisol, the amount of the compound selected from said group being sufficient to enhance the anti-inflammatory activity or duration of action, or both, of loteprednol etabonate, but insufficient to itself have therapeutic action.

DETAILED DESCRIPTION

In the second and third aspects noted above, the enhancing agent [i.e. the compound of formula (I) in the case of the second aspect or hydrocortisone, corticosterone or 11-deoxycortisol in the case of the third aspect] is present in a ratio of about 0.5:1 to about 2:1 by weight relative to the weight of loteprednol etabonate. This weight ratio is roughly equivalent to the corresponding molar ratio but is easier to use in formulating dermatological formulations. Specific useful ratios include about 0.5:1, about 0.75:1, about 1:1, about 1.25:1, about 1.5:1, about 1.75 to 1 and about 2:1. In any event, the amount of the enhancer compound in the third aspect is a subtherapeutic amount when the compound itself has anti-inflammatory activity, that is, it is an amount insufficient to have anti-inflammatory activity. In the case of the compounds of formula (I), the amount is always subtherapeutic because the compounds themselves are inactive.

Among marketed anti-inflammatory steroids, loteprednol etabonate is unique. Designed according to the "inactive metabolite" approach to soft drug design, the locally administered active drug loteprednol etabonate is metabolized in a non-oxidative manner upon reaching the blood-stream and tissues into an inactive metabolite which is itself not only inactive against inflammation but also lacks toxicity. This design has led to the impressive safety profile the drug has exhibited over its thirteen years of marketing for ophthalmic inflammation. Moreover, it is known that, when compared to prednisolone in clinical trials, loteprednol etabonate did not elevate intraocular pressure or cause cataracts. Furthermore, as will be seen from data presented below, unlike other marketed anti-inflammatory steroids, loteprednol etabonate has been found to not significantly decrease skin thickness at appropriate dosage levels and over appropriate time periods, meaning loteprednol etabonate have been found to cause no or minimal skin atrophy under these conditions. This makes loteprednol uniquely well-suited for application to the eyelid and periorbital areas, areas in which the skin is naturally thin and other anti-inflammatory steroids are contraindicated.

When an enhancer of formula (I) is used in the second aspect of the invention, it can be cortienic acid, $\Delta^1$-cortienic acid, cortienic acid methyl ester or $\Delta^1$-cortienic acid methyl ester. Chemically, these compounds can be named 11$\beta$,17$\alpha$-dihydroxyandrost-4-dien-3-one-17$\beta$-carboxylic acid; 11$\beta$,17$\alpha$-dihydroxyandrosta-1,4-dien-3-one-17$\beta$-carboxylic acid; methyl 11$\beta$,17$\alpha$-dihydroxyandrost-4-dien-3-one-17$\beta$-carboxylate; and methyl 11$\beta$,17$\alpha$-dihydroxyandrosta-1,4-dien-3-one-17$\beta$-carboxylate, respectively. In a particular embodiment of the second aspect of the invention, the enhancer is $\Delta^1$-cortienic acid.

In a particular embodiment of the third aspect of the invention, the enhancing compound is hydrocortisone.

The enhancement of loteprednol etabonate's activity or duration of action in various treatments of inflammation, but not in the treatment of eyelid dermatitis, is described in Bodor U.S. Pat. No. 7,560,448 and Bodor U.S. Pat. No. 7,687,484.

In some particular embodiments of the invention, loteprednol etabonate is the sole anti-inflammatory agent in the composition. In yet other particular embodiments, loteprednol etabonate is the sole active ingredient in the composition.

Throughout the instant specification and claims, the following definitions and general statements are applicable.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention. The basic and novel features herein are the provision of a method for the treatment of eyelid dermatitis and/or dermatitis of the periorbital area of a subject in need thereof by applying to the affected area an anti-inflammatory effective amount of loteprednol etabonate (LE), optionally formulated with cortienic acid, $\Delta^1$-cortienic acid, cortienic acid methyl ester, $\Delta^1$-cortienic acid methyl ester, hydrocortisone, corticosterone or 11-deoxycortisol (in an amount sufficient to enhance the anti-inflammatory activity or duration of action of loteprednol etabonate as defined above), formulated into a dermatological composition with a dermatologically effective carrier. The inclusion of materials which would interfere with the anti-inflammatory action of LE (or, in the case of the second and third aspects hereof, which would interfere with the enhancement of LE's anti-inflammatory action) in treating the subject conditions are not encompassed by these terms. Likewise, these terms do not permit inclusion of materials in the applied compositions which would cause skin atrophy or be irritating to the targeted skin areas or encourage infection in these areas or in any other way interfere with the desired treatment.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

As used herein, the term "subtherapeutic amount" means an amount below that expected to have a therapeutic effect in a given combination/composition/method. A subtherapeutic amount can also be defined as an amount of hydrocortisone, corticosterone or 11-deoxycortisol which is itself insufficient to have an anti-inflammatory activity, that is, insufficient to provoke or cause an anti-inflammatory response. Actual amounts vary with the particular compounds involved. For example, loteprednol etabonate (LE) has approximately 20 times the activity of hydrocortisone (HC). Therefore, a ratio of HC:LE of 1:1 or 2:1 utilizes an amount of hydrocortisone which has only $\frac{1}{10}$ or $\frac{1}{20}$ the anti-inflammatory activity of the active ingredient loteprednol etabonate. Such an amount of HC is effective as an enhancer of LE but is not itself a large enough amount to be therapeutic. Rather, the amount is subtherapeutic.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001).

As used herein, "treating" means reducing, hindering or inhibiting the development of, controlling, alleviating and/or reversing the symptoms in the individual treated in accord with the present invention, as compared to the symptoms of an individual not being treated according to the invention. A practitioner will appreciate that the compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods of the present invention are intended for use with any subject/patient that may experience the benefits of the methods of the invention. Thus, in accordance with the invention, the terms "subjects" as well as "patients," "individuals" and "warm-blooded animals" include humans as well as non-human subjects, particularly domesticated animals, particularly dogs, cats, horses and cows, as well as other farm animals, zoo animals and/or endangered species.

Hydrocortisone, corticosterone and 11-deoxycortisol, while themselves much less active as glucocorticoids than loteprednol etabonate and optionally used herein as synergists in amounts lower than amounts considered therapeutically effective, are able to enhance the glucocorticoid activity and/or duration of glucocorticoid action of LE by competing with it in vivo for transcortin binding sites. The addition of the hydrocortisone, corticosterone or 11-deoxycortisol hinders efflux away from the site of local administration (which is also the site of action) of the active anti-inflammatory compound LE by competing with the active compound for various in vivo systems which transport away from the site. This thus contributes to an increase in the amount of free active compound available at the desired site of action/administration or increases the time that the active compound remains at the site, or both. Further details of this mechanism of action are set forth in Bodor U.S. Pat. No. 7,687,484.

The other optional synergists used herein, that is, the compounds of formula (I), are inactive metabolites and do not themselves have glucocorticoid action. However, these compounds also enhance the glucocorticoid activity and/or duration of action of LE by competing with it in vivo for transcortin binding sites. For further details, see Bodor U.S. Pat. No. 7,560,448.

Loteprednol etabonate, optionally together with a compound of formula (I), hydrocortisone, corticosterone or 11-deoxycortisol, can be combined with suitable non-toxic dermatologically acceptable carriers to provide dermatological compositions for use in treating eyelid dermatitis and/or dermatitis of the periorbital area.

Examples of types of preparations especially suitable for administration in accord with the present invention include ointments, gels, creams, lotions and cream gels. Such compositions can be sterile or not sterile. For example, while not essential, a sterile ointment or gel previously described for ophthalmic use or a similar sterile formulation can be readily employed in the instant method.

Ointments and creams or gels or cream gels can, for example, be formulated with an aqueous or oily base with the addition of suitable thickening and/or gelling agents and/or glycols. Such base can thus, for example, include water and/or an oil such as liquid paraffin or a vegetable oil such as arachis oil or castor oil, or a glycolic solvent such as propylene glycol or 1,3-butanediol. Thickening agents which can be used according to the nature of the base include soft paraffin, aluminum stearate, cetostearyl alcohol, polyethylene glycols, woolfat, hydrogenated lanolin and beeswax and/or glyceryl monostearate and/or non-ionic emulsifying agents.

The solubility of the steroid(s) in the ointment or cream can be enhanced by incorporation of an aromatic alcohol such as benzyl alcohol, phenylethyl alcohol or phenoxyethyl alcohol.

Lotions can be formulated with an aqueous or oily base and will in general also include one or more of the following, namely, emulsifying agents, dispersing agents, suspending agents, thickening agents, solvents, coloring agents and perfumes.

In a particular embodiment, an elegantly simple ointment can be applied, which is prepared by combining loteprednol etabonate (optionally in sterile form) with mineral oil and white petrolatum. If desired, an enhancing compound as defined hereinabove can also be included and the final composition can be sterilized.

In another particular embodiment, a cream formulation can be applied, which is prepared by combining loteprednol etabonate (and optionally an enhancing compound as defined above) with ingredients such as glycerin 99% (or other humectant as exemplified below), glyceryl stearate/PEG 100 stearate, cetyl alcohol, stearyl alcohol, oily components such as white petrolatum and light mineral oil, silicones such as dimethicone (50 cst), benzyl alcohol, purified water, carbomers (such as carbomer 940 NF) and trolamine.

In yet other particular embodiments, gel formulations can be applied, which are prepared by combining loteprednol etabonate (if desired together with one of the enhancing compounds herein, such as $\Delta^1$-cortienic acid), together with, for example, a chelator, demulcent(s), or humectant(s), buffering agent, osmolyte, surfactant(s), pH adjuster, preservative(s), vehicle (water) and gelling agent.

The gelling agent can include:

polycarbophil, which is polyacrylic acid crosslinked with divinyl glycol, for example NOVEON® AA-1 polycarbophil, USP;

carbomers, for example CARBOPOL 980 NF marketed by NOVEON;

polymeric emulsifying agents such as PEMULEN, i.e. crosspolymer acrylates/C10-30 alkyl acrylates, for example, PEMULEN TR1, PEMULEN TR2, CARBOPOL 1342, CARBOPOL 1382, CARBOPOL 981 or CARBOPOL ULTREZ;

polysaccharide biopolymers such as xanthan gum;

other gums such as caroub gum or guar gum, or alginates;

modified celluloses such as hydroxyethylcellulose, methylcellulose, hydroxypropylcellulose, hydroxypropylmethylcellulose and carboxymethylcellulose;

starch derived products such as STRUCTURE XL marketed by National Starch; and a mix of polysorbate 80 and isohexadecane and acrylamide/sodium acryloyldimethyltaurate copolymer (such as SIMULGEL 600);

a mixture of polyacrylamide/isoparaffin C13-14/laureth-7 such as SEPIGEL 305 by SEPPIC;

acrylic polymers coupled to hydrophobic claims, such as the PEG-150/decyl/SMDI copolymer sold as ACULYN 44 [polycondensate comprising at least a polyethylene glycol having 150 or 180 mol of ethylene oxide, decyl alcohol and methylenebis (4-cyclohexyl isocyanate (SMDI), at 35% by weight in a mixture of propylene glycol (39%) and water (26%)].

The gels can further include:

humectants or pro-penetrant agents such as propylene glycol or equivalent, for example, glycerin and sorbitol, for example, alkylenes and polyalkylene glycols such as ethylene glycol, polyethylene glycols (liquid), propylene glycol, dipropylene glycol, butylene glycol, pentylene glycol, hexylene glycol. These latter could be oxyethylenated or not. Glycol ethers are also representative such as ethoxydiglycol, diethylene glycol monoethyl ether (tradename TRANSCUTOL HP by GATTEFOSSE), dipelargonate propylene glycol, propylene glycol laurate (tradename LAUROGLYCOL by GATTEFOSSE), Propylene glycol dicaprate dicaprylate (tradename ESTOL 1526 by UNIQEMA); and other pro-penetrants such as fatty esters, fatty acids or fatty alcohols or other alcohols, for example, ethanol, dimethyl isosorbide (tradename ARLASOLVE DMI by UNIQEMA), pyrrolidone methyl (tradename PHARMASOLVE by ISP), oleic acid (tradename OLÉINE V2 by Stéarinerie Dubois), PEG-8 capric/caprylic glycerides (tradename LAERASOL by GATTEFOSSE) and oleic alcohol (tradename HD EUTANOL V PH by COGNIS).

In a specific gel for use herein, in addition to loteprednol etabonate and, if desired, an enhancer such as $\Delta^1$-cortienic acid, the following ingredients can be present: edetate disodium dihydrate (chelating agent), glycerin and propylene glycol (demulcents/humectants/pro-penetrating agents), boric acid (buffer), polycarbophil (gelling or suspending agent), sodium chloride (osmolyte), tyloxapol (surfactant), sodium hydroxide (pH adjuster), benzalkonium chloride (preservative) and water, e.g. water for injection (vehicle).

In another specific gel for use herein, in addition to loteprednol etabonate (and, if desired, an enhancer such as $\Delta^1$-cortienic acid), the dermatological composition comprises a carbomer, disodium edetate, a paraben, a poloxamer, propylene glycol, sodium hydroxide and purified water.

A particular cream is described above. Creams generally comprise, in addition to loteprednol etabonate (and optionally, an enhancer as hereinbefore described, such as $\Delta^1$-cortienic acid), at least one ingredient selected from the following: mineral oils such as perhydrosqualene; silicone oils such as cyclomethicone or dimethicone; siliconed oily components such as siliconed fatty components; non-siliconed fatty components such as vegetable, mineral, animal or synthetic oils; and tensioactive agents or emulsifying agents, preferably such as PEG-20 methyl glucose sequistearate or methyl glucose sequistearate.

Among the non-siliconed oily components, the common oils are representative, such as paraffin oil, Vaseline (or petroleum jelly), white petrolatum, light mineral oil, almond oil, perhydrosqualene, apricot oil, wheat germ oil, sweet almond oil, calophyllum oil, palm oil, castor oil, avocado oil, jojoba oil or olive oil, fatty acid esters or fatty alcohol esters such as dodecyl octyl octanoates, alcohols or polyalcohol decanoates or ricinoleates; fatty acid triglycerides; glycerides; hydrogenated polyisobutene, solid at room temperature hydrogenated oils; lanolines; solid at room temperature fatty esters; adipate diisopropyl (tradename CRODAMOL DA by Croda), PPG 15 stearyl ether (tradename ARLAMOL E by UNIQEMA), octyl dodecanol (tradename EUTANOL G by COGNIS), Caprylic/capric triglycerides (tradename MIGLYOL 812N by SPCI), C12-C15 alkyl benzoate (tradename TEGOSOFT TN by Degussa).

As tensioactive agents or as emulsifying agents, several components are representative, such as PEG-20 methyl glucose sequistearate (tradename GLUCAMATE SSE 20 by Amerchol) or methyl glucose sesquistearate (tradename GLUCATE SS by Amerchol), unsaturated or saturated fatty acid esters, oleic acid or isostearic acid such as polyglycerin and isostearic acid esters (tradename LAMEFORM TGI by SIDOBRE-SINNOVA HENKEL), sorbitan isostearate (tradename ARLACEL 987 by UNIQEMA), sorbitan sesquioleate (tradename ARLACEL 83 by UNIQEMA), sorbitan laurate (tradename SPAN 20 by UNIQEMA), glycol and isostearic acid esters such as PEG-6 isostearate (tradename OLEPAL ISOSTEARIQUE by GATTEFOSSE), sorbitol and oleic acid esters such as polysorbates (tradename TWEEN by UNIQEMA), fatty alcohol ethers such as oleic acid and particularly glycol and oleic acid esters such as oleths (tradename BRIJ by UNIQEMA), oxyethylenated sorbitan monostearate, fatty alcohols such as stearyl alcohol or cetyl alcohol and particularly selected from among macrogol 21 stearyl ether (tradename BRIJ 721 by UNIQEMA), macrogol 2 stearyl ether (tradename BRIJ 72P by UNIQEMA), glyceryl/PEG 100 stearate (tradename ARLACEL 165FL by UNIQEMA), ceteareth 20 (tradename EUMULGIN B2 by COGNIS), PEG-6 and PEG 32 palmitostearate (tradename TEFOSE 1500 by GATTEFOSSE).

In addition, cream gels (or gel creams) can be prepared by selecting ingredients appropriate for each of these formulations, as will be illustrated below.

The lotions that can be used herein, in addition to loteprednol etabonate and, if desired, one of the above-defined enhancers, for example, $\Delta^1$-cortienic acid, can comprise at least one of the following:

humectant agents or pro-penetrant agents such as propylene glycol (or equivalent such as glycerin and sorbitol), polyethylene glycol, PEG400;

mineral oils such as perhydrosqualene as previously described;

lipophilic components such as caprylic/capric triglycerides as previously described; and emulsifying agents such as previously described, for example, PEG-20 methyl glucose sequistearate and methyl glucose sequistearate.

In the compositions administered herein, loteprednol etabonate (LE) is present in an amount of from about 0.05% to about 2.0%, preferably in an amount of from about 0.17 to about 1.0% and even more preferably in an amount of from about 0.1% to about 0.5%, especially about 0.1%, about 0.15%, about 0.2%, about 0.25%, about 0.3%, about 0.35%, about 0.4%, about 0.45% or about 0.5%. When an enhancer is present as described hereinabove, the amount of enhancer is in a weight ratio to the LE as described hereinabove. Typically, to treat eyelid dermatitis and/or dermatitis of the periorbital area, the composition is applied once or twice daily, gently and evenly, covering the affected area thinly.

The pharmaceutical compositions according to the invention may also comprise inert additives or combinations thereof, such as: wetting agents; flavor enhancers; preservatives, such as para-hydroxybenzoic acid esters; stabilizers; moisture regulators; pH regulators; osmotic pressure modifiers; emulsifiers; and antioxidants, such as α-tocopherol, butyihydroxyanisole, butylhydroxytoluene, superoxide dismutase, ubiquinol or certain metal chelating agents.

It is apparent that care will be taken to select the optional compound(s) to be added to these compositions in such a way that the advantageous properties intrinsically associated with the present invention are not, or are not substantially, adversely affected by the envisaged addition.

It has been found that use of the enhancing agent $\Delta^1$-cortienic acid is particularly advantageous because it surprisingly stabilizes the LE between one and one-half and two times relative to LE in the absence of the enhancer. Accordingly, the gels, ointments, creams, cream gels and lotions which additionally contain this particular enhancing agent are especially useful in the treatment of eyelid dermatitis and dermatitis of the periorbital area.

To investigate the effect of $\Delta^1$-cortienic acid ($\Delta^1$-CA) on the stability of loteprednol etabonate (LE), the following experiments were conducted at room temperature (22.5° C.):

Method

Compound—LE (MW 466.5), $\Delta^1$-CA (MW 346.4)

Suspension Formulation

Active: LE, 0.1% (2.144 mM) and 0.2% (4.288 mM)

Inactives: $\Delta^1$-CA, 0.1% (2.897 mM) & 0.2% (5.795 mM); Glycerin, Povidone, Tyloxapol, Edetate Disodium Dihydrate, Purified Water.

Preservative added: Benzalkonium Chloride 0.01%

Suspension Preparation

1) To the mixture of 9.32 g glycerin (USP, 99.7%), 7.2 g Povidone (USP, 90000), 1.2 g Tyloxapol (USP), 0.08 g benzalkonium chloride (USP, 40 µl of 50% solution), and 0.04 g Edetate Disodium Dihydrate (USP), 400 ml Purified Water (USP) was added. 2) The mixture was sonicated for 20 minutes to make a homogenous solution, and its pH was measured. 3) To 150 ml of each solution was added 0.15 g or 0.3 g of loteprednol etabonate (micronized), and the mixture was sonicated for 30 minutes to obtain two LE-only suspensions at 0.1% & 0.2%, respectively. 4) From each LE-only suspension (0.1 & 0.2%), 75 ml was taken and combined with micronized $\Delta^1$-CA (0.075 & 0.15 g). 5) All four suspensions were mixed and sonicated again for another 30 minutes, and the pH of each was measured (Blank vehicle pH 3.4; LE only suspensions, pH 3.5; LE+$\Delta^1$-CA suspensions, pH 3.3). 6) Each of the four suspensions was separated/pipetted (1 ml) into 8 ml amber vials (1 ml/vial) and the vials were sealed with caps and parafilm. 7) Half of each formula 1 ml/vial samples were loaded on a shaker for continuous shaking (170 times/min), and the other half of the samples were only shaken vigorously by hand each time before HPLC sample preparation. 8) For periodical samplings, one sample of every set of suspensions was taken and analyzed by HPLC. 9) All procedures were conducted at 22.5° C.

Sample Preparation

The change of LE and its degradation products AE (acid etabonate) and $\Delta^1$-CA in the suspensions was measured periodically. A vial of each series of suspensions was randomly taken, mixed/washed with 50% acetonitrile, and transferred to a 10 ml cylinder to make a final volume of 10 ml solution (about 100 µg/ml for LE 0.1% or 200 µg/ml for LE 0.2% samples).

HPLC

A HPLC system operating at ambient temperature was used to quantitative determination of LE, AE and $\Delta^1$-CA. Phenonemax Luna C18 (5µ, 150×4.6 mm) was connected to a Spectra-Physics component system consisting of a SP 8810 precision isocratic pump, a Rheodyne 7125 injector (injection volume 20 µl), a SP 8450 UV/VIS variable wavelength detector (operated at 254 nm), and a SP 4290 integrator. At a flow rate of 1 ml/min, a mobile phase consisting of acetonitrile, acetic acid, and water in a volume ratio of 60:0.2:40 eluted LE, AE and $\Delta^1$-CA at 7.5, 3.2, and 2.2 min, respectively. Each sample was run in triplicate. The change in peak-area was recorded, and the percent ratio of each compound (LE, AE, and $\Delta^1$-CA) toward total (LE+AE+$\Delta^1$-CA) in peak-area was used to evaluate the disappearance of LE as well as the appearance of AE and $\Delta^1$-CA. Since $\Delta^1$-CA was used as an additive for LE+$\Delta^1$-CA samples, the appearance of $\Delta^1$-CA (from AE) was in the error range of these samples, and furthermore, in the LE-only samples, $\Delta^1$-CA was observed from zero-time at 0.36±0.19% of total (LE+AE+$\Delta^1$-CA), and less than, or about 0.5% thereafter in all LE-only samples; the number 0.5% was used as the amount of $\Delta^1$-CA for all of LE+$\Delta^1$-CA samples.

Results & Discussion

The stability study was followed for 421 days. In the shaker-shaking samples, some solids formation that stuck on the glass wall of the vials was observed. However, there was no difference in HPLC results between continuous shaker-shaking and periodical hand shaking, thus, six samples with the same formulation were combined, and the results are shown in the following Table 1.

At both LE 0.1% and 0.2% levels, addition of the same levels of $\Delta^1$-CA clearly increased LE stability. The degradation of LE resulted in a steady increase in AE. However, $\Delta^1$-CA remained at a similar level (about 0.5% or less), indicating that AE was stable in this type of suspension.

The degradation/hydrolysis of LE follows first-order kinetics with half-lives ($t_{1/2}$) of 28.38 and 43.31 years ($t_{95}$ of 2.10 and 3.21 years) for LE 0.1 and 0.2% suspensions, respectively (Table 1). By addition of the same concentration of $\Delta^1$-CA in the suspensions, the half-lives increased to almost two times. Thus, half-lives of 49.44 and 82.65 years ($t_{95}$ of 3.66 and 6.12 years) for LE 0.1%+$\Delta^1$-CA 0.1% suspension and for LE 0.2%+$\Delta^1$-CA 0.2% suspension, respectively, have been achieved.

Comparing the stability changes in terms of concentration, the results indicate that in either LE-only, or LE+$\Delta^1$-CA suspension, the increase in concentration (from 0.1% to 0.2%) stabilized LE by more than 1.5 times.

Conclusion

The increasing effect of $\Delta^1$-CA (0.1% & 0.2%) on the stability of LE (0.1% & 0.2%) in aqueous suspension at room temperature (22.5° C.) has been demonstrated.

TABLE 1

Stability of LE (0.1 & 0.2%) in the suspensions containing 0, 0.1 & 0.2% of $\Delta^1$-Cortienic Acid

| | LE | | | |
|---|---|---|---|---|
| | 0.1% | 0.1% | 0.2% | 0.2% |
| $\Delta^1$-CA | — | 0.1% | — | 0.2% |
| k (day$^{-1}$ × 10$^{-5}$) | 6.69 | 3.84 | 4.38 | 2.30 |
| t$_{1/2}$ (year) | 28.38 | 49.44 | 43.31 | 82.65 |
| t$_{95\%}$ (year) | 2.10 | 3.66 | 3.21 | 6.12 |
| r | 0.992 | 0.980 | 0.998 | 0.975 |

To investigate the effects of loteprednol etabonate (LE) on skin atrophy and thymus weight, the following experiments were conducted:

Materials and Methods

Reagents and Test Materials

Loteprednol etabonate (LE) and betamethasone valerate (BMV) were formulated by Otsuka Pharmaceuticals at a concentation of 0.1% in a white petrolatum base containing 5% propylene carbonate. All other test materials were steroidal anti-inflammatory compounds [Locoid® or hydrocortisone 17-butyrate (HCB) and Rinderon® or betamethasone 17-valerate (BMV-R) or white petrolatum vehicle as a control] which were commercially available in Japan at the time of testing.

Animal Care

Sprague-Dawley rats were used in this study. All animals were from the animal research facilities of Otsuka Pharmaceutical Co. Ltd., Tokushima, Japan and all animal care and housing were according to their standard procedures.

Experimental Design

Groups of male rats (Sprague Dawley) weighing about 200-240 g were shaved on the dorsal surface. Loteprednol etabonate and betamethasone 17-valerate were administered as 0.1% ointments using white petrolatum base containing 5% propylene carbonate (PC). In separate groups, 0.12% betamethasone 17-valerate (Rinderon®), 0.1% hydrocortisone 17-butyrate (Locoid®) were administered as comparators. White petrolatum base (+5% PC) was administered to control animals.

Two schedules of dosing were used: 200 mg/rat for 14 days (n=5) or 400 mg/rat for 7 days (n=7). At the end of these periods, rats were sacrificed. The thickness of a 1 cm² section of skin from the treated area was measured. The thymus was removed and weighed.

Results

The results are summarized in Table 2. Betamethasone valerate, either in the same vehicle as loteprednol etabonate or in a commercial preparation, produced the most significant decreases in thymus weight. Hydrocortisone butyrate in a commercial preparation also caused significant decreases in thymus weight. Skin atrophy was most marked with hydrocortisone 17-butyrate in terms of both skin weight and thickness. The commercial preparation of betamethasone valerate did not produce skin atrophy by either parameter. Loteprednol etabonate did not cause a statistically significant decrease in skin thickness in either regimen.

TABLE 2

Effect of loteprednol etabonate (LE), betamethasone valerate (BMV and BMV-R) and hydrocortisone butyrate (HCB) on skin atrophy and thymus weight in rats

| | | PERCENT DECREASE IN | |
|---|---|---|---|
| Drug | Dosing Schedule | THYMUS WEIGHT | SKIN THICKNESS |
| LE (0.1%) | 200 mg/day - 14 d | 12.8 | 6.5 |
| BMV (0.1%) | 200 mg/day - 14 d | 70.1** | 12.8* |
| HCB (0.1%) | 200 mg/day - 14 d | 29.5* | 17.9* |
| BMV-R (0.12%) | 200 mg/day - 14 d | 53.5** | 6.9 |
| LE (0.1%) | 400 mg/day - 7 d | −2.5 | 10.3 |
| HCB (0.1%) | 400 mg/day - 7 d | 36.0** | 12.8* |

*p < 0.05 vs controls
**p < 0.01 vs controls

CONCLUSION

Under experimental conditions where both hydrocortisone 17-butyrate and betamethasone 17-valerate caused skin atrophy and significant decreases in thymus weight, loteprednol etabonate caused less skin atrophy and did not effect thymus weight significantly. Anti-inflammatory activity has previously been demonstrated with the concentration of loteprednol etabonate used in this study.

LE was thus found to have minimal effects on skin atrophy and thymus weight in the testing described above. The minimal skin atrophy demonstrated by LE is very unexpected because this drug has strong anti-inflammatory activity, yet other even less active anti-inflammatory glucocorticoids cause much more skin atrophy. The separation in these effects enables LE to be useful in treating eyelid dermatitis and dermatitis of the periorbital area in which other marketed anti-inflammatory steroids cannot be used because they cause much greater skin atrophy.

To investigate photocarcinogenicity, a multi-week study of loteprednol etabonate cream in hairless mice, with or without simulated sunlight, was undertaken. The study was undertaken for a thirteen-week period and did not show carcinogenicity. Because effects on skin atrophy were also recorded, however, and because a period of 4 weeks is the maximum recommended treatment period for eyelid dermatitis, results for the first 4 weeks of the study are given below. Mice were treated with the cream formulation once daily, five days per week. In the portion of the test summarized below, the cream contained LE in amounts of 0, 0.25% by weight and 0.5% by weight. (Higher concentrations were tested but results are not given here). Week 0 was baseline. After 4 weeks, skin thickness measurements were taken using a caliper. The cream also contained glycerin 99% USP, benzyl alcohol NF, purified water USP, carbomer 940 NF (Carbopol 980), glyceryl stearate/PEG 100 stearate, trolamine 99F, cetyl alcohol NF, stearyl alcohol NF, white petrolatum USP, light mineral oil NF and dimethicone (50 cst).

TABLE 3

Multi-week Topical Study of Loteprednol Etabonate Cream in Hairless Mice, With or Without Simulated Sunlight
Skinfold Thickness - Summary - Male Mice

|  |  | Group | | | |
| --- | --- | --- | --- | --- | --- |
|  |  | 1 | 2 | 3 | 4 |
| Descriptor a |  | Untreated | Loteprednol Etabonate Cream | Loteprednol Etabonate Cream | Loteprednol Etabonate Cream |
| MCL/Mouse |  | N/A | 0 (Vehicle) | 0.25 | 0.5 |
| UVR (RBU/Week) |  | N/A | 0 | 0 | 0 |
| Mice Tested | N | 6 | 6 | 6 | 6 |
| Week 0 | Mean ± S.D. | 0.80 ± 0.04 | 0.81 ± 0.05 | 0.75 ± 0.03 | 0.78 ± 0.05 |
| Week 4 | Mean ± S.D. | 0.89 ± 0.06 | 0.86 ± 0.04 | 0.71 ± 0.06** | 0.77 ± 0.06* |
|  |  | Group | | | |
|  |  | 7 | 8 | 9 | 10 |
| Descriptor a |  | Untreated | Loteprednol Etabonate Cream | Loteprednol Etabonate Cream | Loteprednol Etabonate Cream |
| MCL/Mouse |  | N/A | 0 (Vehicle) | 0.25 | 0.5 |
| UVR (RBU/Week) |  | 600 | 600 | 600 | 600 |
| Mice Tested | N | 6 | 6 | 6 | 6 |
| Week 0 | Mean ± S.D. | 0.79 ± 0.07 | 0.75 ± 0.06 | 0.77 ± 0.04 | 0.81 ± 0.06 |
| Week 4 | Mean ± S.D. | 0.92 ± 0.06 | 0.94 ± 0.08 | 0.81 ± 0.08# | 0.83 ± 0.07 | a Formulation administration occurred once daily, five days per week.
*Significantly different from the Group 1 value ($p \leq 0.05$).
**Significantly different from the Group 1 value ($p \leq 0.01$).
Groups 3 and 4, at LE concentrations of 0.25% by weight and 0.5% by weight, respectively, showed no or minimal skin atrophy after treatment for 4 weeks.
Significantly different from the Group 7 value ($p \leq 0.05$).
Groups 7 and 8, at LE concentration of 0.25% by weight and 0.50% by weight, respectively, showed no or minimal skin atrophy after 4 weeks.

TABLE 4

Multi-week Topical Study of Loteprednol Etabonate Cream in Hairless Mice, With or Without Simulated Sunlight
Skinfold Thickness - Summary - Female Mice

|  |  | Group | | | |
| --- | --- | --- | --- | --- | --- |
|  |  | 1 | 2 | 3 | 4 |
| Descriptor a |  | Untreated | Loteprednol Etabonate Cream | Loteprednol Etabonate Cream | Loteprednol Etabonate Cream |
| MCL/Mouse |  | N/A | 0 (Vehicle) | 0.25 | 0.5 |
| UVR (RBU/Week) |  | N/A | 0 | 0 | 0 |
| Mice Tested | N | 6 | 6 | 6 | 6 |
| Week 0 | Mean ± S.D. | 0.75 ± 0.09 | 0.72 ± 0.06 | 0.76 ± 0.11 | 0.81 ± 0.12 |
| Week 4 | Mean ± S.D. | 0.73 ± 0.04 | 0.75 ± 0.04 | 0.67 ± 0.07 | 0.67 ± 0.05 |
|  |  | Group | | | |
|  |  | 7 | 8 | 9 | 10 |
| Descriptor a |  | Untreated | Loteprednol Etabonate Cream | Loteprednol Etabonate Cream | Loteprednol Etabonate Cream |
| MCL/Mouse |  | N/A | 0 (Vehicle) | 0.25 | 0.5 |
| UVR (RBU/Week) |  | 600 | 600 | 600 | 600 |
| Mice Tested | N | 6 | 6 | 6 | 6 |
| Week 0 | Mean ± S.D. | 0.79 ± 0.14 | 0.77 ± 0.12 | 0.77 ± 0.13 | 0.84 ± 0.10 |
| Week 4 | Mean ± S.D. | 0.73 ± 0.06 | 0.80 ± 0.06# | 0.67 ± 0.03 | 0.68 ± 0.04 | a Formulation administration occurred once daily, five days per week.
Groups 3 and 4, at LE concentrations of 0.25% by weight and 0.50% by weight, respectively, showed no significant skin atrophy after treatment for 4 weeks.
Significantly different from the Group 7 value ($p \leq 0.05$).
Groups 7 and 8, at LE concentrations of 0.25% by weight and 0.50% by weight, respectively, showed no or minimal skin atrophy after 4 weeks.

When the dosage levels were increased to 1.5% by weight and 4.5% by weight of LE and/or the study was extended to week 8 and to week 13, more skin atrophy was seen, but such conditions are not analogous to those used in treating eyelid dermatitis.

The results thus indicate no or minimal deleterious effect on skin thickness caused by LE at 0.25% and 0.5% after application for four weeks. This confirms the results for LE described in the Japanese studies detailed above.

Further confirmation has been found in a patient with necrobiosis. Topical treatment with a standard anti-inflammatory steroid, betamethasone valerate, was successful in lessening inflammation but thinned the skin. In contrast, LE applied topically in a 0.5% cream (described in Example 2 below) was effective in treating the necrobiosis by lessening inflammation but did not cause skin atrophy.

The following Examples illustrate numerous formulations useful in the method of treatment of the present invention. These formulations are merely illustrative and not limitative of the remainder of the specification and claims in any way whatsoever.

In these Examples and throughout this description, percentages are by weight unless otherwise noted.

Example 1

An ointment is prepared having the following composition:

| Ingredient | Concentration (mg/g) | % w/w |
|---|---|---|
| Loteprednol etabonate (LE), optionally sterile | 5.0 | 0.5 |
| Mineral oil | 145.0 | 14.5 |
| White Petrolatum | 850.0 | 85.0 |

The LE is added to a heated mixture of the petrolatum and mineral oil, then homogenized. Alternatively and preferably, the amount of optionally sterile LE can be reduced to 2.0 mg/g together with adding 2.0 mg/g of optionally sterile $\Delta^1$-cortienic acid ($\Delta^1$-CA) or other enhancer to the ointment, to give an ointment containing 0.2% w/w LE and 0.2% w/w $\Delta^1$-CA. If desired, the product is maintained in sterile form during manufacturing. The formulation is inherently bacteriostatic, allowing a preservative-free formulation.

Example 2

A 0.5% LE cream is prepared having the following composition:

| Ingredient | Amount (Kg/50 Kg) | % w/w |
|---|---|---|
| Glycerin 99% USP | 2.50 Kg | 5.00 |
| Loteprednol Etabonate (LE) | 250 g | 0.500 |
| Glyceryl Stearate (and) PEG 100 Stearate | 4.00 Kg | 8.00 |
| Cetyl Alcohol NF | 0.50 Kg | 1.00 |
| Stearyl Alcohol NF | 0.50 Kg | 1.00 |
| White Petrolatum USP | 5.00 Kg | 10.0 |
| Light Mineral Oil NF | 5.00 Kg | 10.0 |
| Dimethicone (50 cst) | 250 g | 0.500 |
| Benzyl Alcohol NF | 0.50 Kg | 1.00 |
| Purified Water USP* | 31.74 Kg | 63.475 |
| Carbomer 940 NF (Carbopol 980) | 0.15 Kg | 0.300 |
| Purified Water USP | 0.5 L/Kg | 1.00 |
| Trolamine 99 NF | 113 g | 0.225 |

*1% overage added for evaporation losses

A 0.25% LE cream has approximately the same formula except the quantity of LE is 125 grams.

A similar cream including an enhancing agent, e.g. $\Delta^1$-CA, contains 0.2% LE (100 g) and 0.2% $\Delta^1$-CA (100 g).

A 50 Kg batch of the 0.5% LE cream is prepared as described below. The bulk compounding is carried out in an active phase kettle (10.0 L capacity), placed under a Dissolver (15 HP), with a 3 inch standard blade. Glycerin 99 USP (2.5 Kg) is added and mixed to form a vortex, during which time the loteprednol etabonate is added and mixed until it is smooth with no agglomerate present.

The following ingredients are added to the oil base/primary compounding kettle (70 L capacity) without mixing:
Glyceryl Stearate and PEG-100 Stearate (4.00 Kg)
Cetyl Alcohol NF (0.50 Kg)
Stearyl Alcohol USP (5.00 Kg)
White Petrolatum USP (5.00 Kg)
Light Mineral Oil NF (5.00 Kg).

The mixture is heated to 73-77° C. and mixed until clear. Dimethicone (250 g) and benzyl alcohol NF (0.50 Kg) are added, and mixed until uniform while maintaining the temperature of 73-77° C.

Thirty one liters of purified water are poured into a water phase kettle (70 L capacity) and placed under a dissolver (20-50 mp) with a 6 inch dispersator blade. Mixing to form a vortex is begun and Carbomer 940 NF (0.15 Kg) is added. The mixture was heated to 78-82° C. while mixing until no lumps are present.

The water phase is then added to the oil phase while mixing. Mixing is continued for 3-5 minutes until the phases are combined. The batch is moved to a dissolver with a 6 inch dispersator blade and mixed for 5-10 minutes until homogeneous.

The batch is placed under a counter motion mixer and mixed while cooling. When the temperature reaches 48-50° C. the active phase is added with continued mixing and cooling. A solution of purified water USP (0.5 L) and trolamine 99 NF (113 g) is prepared and added to the batch when the temperature reaches 40-42° C. Mixing is continued for at least 60 minutes while cooling to 30-33° C.

The percent yield is calculated (by weight) and samples from the top and bottom are submitted for QA analysis. The product is transferred to a holding tank until all QA is completed. The product is then transferred to a filler tank which has been cleaned and sanitized. The product is filled into containers.

The cream is stable for at least one year at room temperature and at 40° C.

Example 3

A gel is prepared having the following composition:

| Ingredient | Concentration | |
|---|---|---|
| | Amount (mg/g) | % w/w |
| Loteprednol Etabonate (LE) | 5.00 | 0.500 |
| Edetate Disodium Dihydrate USP | 0.55 | 0.055 |
| Glycerin USP | 8.80 | 0.880 |
| Propylene Glycol USP | 4.40 | 0.440 |
| Boric Acid NF | 5.00 | 0.500 |
| Polycarbophil USP | 3.75 | 0.375 |
| Sodium Chloride USP | 0.50 | 0.050 |
| Tyloxapol USP | 0.50 | 0.050 |
| Sodium Hydroxide (2N) | 16.85 | 1.685 |

-continued

| Ingredient | Concentration | |
|---|---|---|
| | Amount (mg/g) | % w/w |
| Benzalkonium Chloride Solution, 50% USP | 0.06** | 0.006** |
| Water for Injection USP | qs to 1 g | qs |

**Label claim for BAK is 30 ppm or 0.003%.
*The 2N sodium hydroxide solution is made using sodium hydroxide pellets, NF and water for injection USP.

If desired, manufacturing occurs in an aseptic processing facility in accordance with cGMP and the drug substance, loteprednol etabonate, is sterilized by gamma irradiation prior to use while packaging components are sterilized with ethylene oxide prior to use. This finished gel can also be sterilized, if desired.

This gel can be modified, for example, by using 2.00 mg/g of LE (0.20% w/w), alone or preferably together with an enhancing amount of one of the enhancing agents herein, for example, $\Delta^1$-CA, for example, in an amount of 2.00 mg/g (0.2% w/w).

Example 4

Another aqueous gel for use herein can have the following formula:

| Ingredient | Amount |
|---|---|
| Loteprednol Etabonate (LE) | 5 mg |
| Carbomer 940 (Carbopol 980 NF) or other carbomer | 11 mg |
| Disodium Edetate | 1 mg |
| Methyl Paraben or Eethyl Paraben | 2 mg |
| Poloxamer, e.g. Poloxamer 124 | 2 mg |
| Propylene Glycol | 40 mg |
| Sodium Hydroxide | amount required to obtain a pH level of 5.0 +/− 0.3 |
| Purified Water | q.s. 1 g |

This formula can be modified to contain a different amount of LE, e.g., 2 mg, and/or to also include an enhancer as defined herein such as $\Delta^1$-CA, for example, 2 mg of $\Delta^1$-CA in the case of using 2 mg of LE.

Example 5

An exemplary lotion formulation is as follows:

| Ingredient | % w/w |
|---|---|
| Loteprednol Etabonate (LE) | 0.2 or 0.5 mg |
| Methyl Paraben | 0.15 |
| Simulgel 600 PHA | 1.00 |
| Steareth 21 | 3.00 |
| Glyceryl and PEG 100 Stearate | 3.00 |
| Disodium Edetate | 0.10 |
| Propyl Paraben | 0.05 |
| Perhydrosqualene | 5.00 |
| Cetearyl Isonananoate | 5.00 |
| Sodium Hydroxide 10% | q.s. pH 5.5 ± 0.5 |
| Purified Water | q.s. 100 |

This formula is preferably modified to include an enhancer such as $\Delta^1$-CA, for example 0.2% w/w $\Delta^1$-CA with 0.2% w/w LE.

Example 6

An exemplary cream formulation is as follows:

| Ingredient | Amount |
|---|---|
| Loteprednol Etabonate (LE) | 2 mg or 5 mg |
| Carbomer 934 (BF Goodrich Carbopol 974) | 4.5 mg |
| Disodium Edetate | 1 mg |
| PEG 20 Methyl Glucose Sesquistearate | 35 mg |
| Methyl Glucose Sesquistearate | 35 mg |
| Glycerol | 30 mg |
| Methyl Paraben | 2 mg |
| Cyclomethicone | 130 mg |
| Perhydrosqualene | 60 mg |
| Phenoxyethanol | 5 mg |
| Propyl Paraben | 1 mg |
| Sodium Hydroxide | quantity required for pH 6.5 +/− 0.3 |
| Purified Water | q.s. 1 g |

Alternatively and preferably, LE 2 mg plus $\Delta^1$-CA 2 mg or other enhancing compound herein are substituted in the above formula for the LE used.

Example 7

Another lotion formulation is as follows:

| Ingredient | (% w/w) |
|---|---|
| Loteprednol Etabonate (LE) | 0.2 or 0.5 |
| Disodium EDTA | 0.1 |
| Methyl Paraben | 0.2 |
| Glycerin | 7.0 |
| Carbopol 981 NF | 0.15 |
| Propyl Paraben | 0.1 |
| Ceteareth 20 | 3.0 |
| Stearyl Alcohol | 2.0 |
| Caprylic/Capric Triglycerides | 7.0 |
| Glyceryl and PEG 100 Stearate | 3.0 |
| Cyclomethicone 5 | 6.0 |
| Poloxamer 124 | 0.2 |
| Propylene Glycol | 4.0 |
| Simulgel 600 PHA | 1.0 |
| Aq. Solution of NaOH 10% | 0.4 |
| Purified Water | q.s. 100 |

Yet other lotions preferably substitute 0.2% w/w LE plus from 0.1% w/w to 0.3% w/w, preferably 0.2% w/w, of $\Delta^1$-CA or hydrocortisone (HC) or other enhancer as defined herein, for the LE used above.

Example 8

Yet another lotion formulation is as follows:

| Ingredient | (% w/w) |
|---|---|
| Loteprednol Etabonate (LE) | 0.2 to 0.5 |
| EDTA Disodium | 0.1 |
| Methyl Paraben | 0.2 |
| Carbopol 980 NF | 0.15 |
| Carbopol 981 NF | 0.3 |
| Glycerin | 3.0 |
| Phenoxyethanol | 1.0 |
| Propyl Paraben | 0.2 |
| Methyl Glucose Sesquistearate | 1.0 |
| PEG 20 Methyl Glucose Sesquistearate | 5.0 |
| Caprylic/Capric Triglycerides | 6.0 |
| Dimethicone 20 cst | 1.0 |

-continued

| Ingredient | (% w/w) |
|---|---|
| Poloxamer 124 | 0.2 |
| Propylene Glycol | 4.0 |
| Sodium Hydroxide 10% (w/w) | 0.8 |
| Purified Water | q.s. 100 |

This formulation is alternatively and preferably prepared to contain, for example, 0.2% w/w LE and 0.2% w/w $\Delta^1$-CA or HC in place of the 0.2 to 0.5% LE.

Example 9

An aqueous gel can be prepared having the following composition:

| Ingredient | Amount |
|---|---|
| Loteprednol Etabonate (LE) | 2 mg |
| $\Delta^1$-CA | 2 mg |
| Xanthan Gum | 8 mg |
| Hydroxypropylethylcellulose | 10 mg |
| Disodium Edetate | 1 mg |
| Methyl Paraben (or other paraben) | 2 mg |
| Phenoxyethanol | 10 mg |
| Poloxamer, e.g. Poloxamer 124 | 2 mg |
| Propylene Glycol | 40 mg |
| Purified Water | q.s. 1 g |

Example 10

A cream gel can be prepared having the following composition:

| Ingredient | Amount |
|---|---|
| Loteprednol Etabonate (LE) | 2 mg |
| $\Delta^1$-CA | 2 mg |
| Simulgel 600 PHA | 20 mg |
| Cetearyl Isononanoate | 100 mg |
| Disodium Edetate | 1 mg |
| Methyl Paraben | 2 mg |
| Poloxamer, e.g. Poloxamer 124 | 2 mg |
| Propylene glycol | 40 mg |
| Purified water | q.s. 1 g |

If desired, in place of 2 mg of $\Delta^1$-CA, more LE can be used, for example, a total of 5 mg LE. Alternatively, if desired, 2 mg LE can be used together with 2 mg HC.

Example 11

Another cream gel formulation is as follows:

| Ingredient | Amount |
|---|---|
| Loteprednol Etabonate (LE) | 2 mg or 5 mg |
| Pemulen TR1 | 5 mg |
| Mineral Oil | 120 mg |
| Disodium Edetate | 1 mg |
| Methyl Paraben | 2 mg |
| Propyl Paraben | 1 mg |
| Poloxamer, e.g. Poloxamer 124 | 2 mg |
| Propylene Glycol | 40 mg |
| Sodium Hydroxide | amount required to obtain pH 5.0 +/− 0.3 |
| Purified Water | q.s. 1 g |

Preferably, when 2 mg of LE is present, 2 mg of enhancer, preferably $\Delta^1$-CA, is added to the formulation.

Example 12

A dermal ointment is prepared having the following composition:

| Ingredient | % w/w |
|---|---|
| Loteprednol Etabonate (LE) | 0.2% w/w |
| $\Delta^1$-CA | 0.2% w/w |
| Liquid Paraffin | 10.0% w/w |
| White Soft Paraffin | 88.8% w/w |

Alternatively, $\Delta^1$-CA can be eliminated from the formulation and a larger amount of LE can be used, for example 0.5% w/w, or a different amount of $\Delta^1$-CA or different enhancer can be present within the weight ratios defined hereinabove, and the amount of white soft paraffin adjusted as necessary.

The above exemplified compositions and other compositions for administration according to the present method can be conveniently formulated, for example using known techniques.

Another example is an optionally sterile antibiotic and loteprednol etabonate combination ointment. Each gram of ointment contains: as active ingredients, tobramycin 0.3% (3 mg) and LE 0.2% (2 mg); as synergist, $\Delta^1$-CA or its methyl ester, 0.1% (1 mg) to 0.4% (4 mg), preferably 0.2% (2 mg); as preservative, chlorobutanol, 0.5%, and as inactives, mineral oil and white petrolatum. If desired, the ointment can be prepared without including the synergist.

Yet another ointment can be formulated to contain an antibacterial and LE as follows: as actives, sulfacetamide sodium, 10% and LE, 0.2%; as synergist, $\Delta^1$-cortienic acid, 0.1% to 0.4%, preferably 0.2% when present; as preservative, phenylmecuric acetate (0.0008%); and as inactives, mineral oil, white petrolatum, and petrolatum and lanolin alcohol.

Another cream or lotion can be formulated to contain, in each gram thereof: 0.5 mg or 0.2 mg of LE and, preferably, 0.2 to 2.0 mg of $\Delta^1$-cortienic acid, in a hydrophilic cream or lotion base consisting of purified water, mineral oil, white petrolatum, cetearyl alcohol 70/30, ceteareth 30, propylene glycol, sodium phosphate monobasic monohydrate and phosphoric acid, with benzyl alcohol as a preservative. If necessary, the cream or lotion may contain sodium hydroxide.

It will be apparent from the foregoing that, in light of the lack of substantial skin atrophy occasioned by loteprednol etabonate, the composition described herein can also be administered in methods for the treatment of dermatitis of other areas in which the skin is thin, such as the face, by applying to the affected area of the skin of a subject in need of such treatment, an anti-inflammatory effective amount of a composition as described herein.

While the foregoing has been described in terms of various preferred embodiments, the skilled artisan will appreciate that various modifications, substitutions, omissions and changes may be made without departing from the spirit thereof. Therefore, the scope of the invention is limited solely by the scope of the following claims, including equivalents thereof.

What is claimed is:

1. A method for the treatment of eyelid dermatitis and/or dermatitis of the periorbital area, which comprises applying to the eyelid and/or periorbital area, respectively, of a subject in need of such treatment, an anti-inflammatory effective amount of a dermatological composition comprising loteprednol etabonate and a dermatologically acceptable carrier therefor, said method being carried out at a dosage level of loteprednol etabonate of from about 0.2% to about 0.5% by weight of the composition once a day for five days per week for four weeks.

2. The method according to claim 1, wherein said composition further comprises:
a compound having the formula

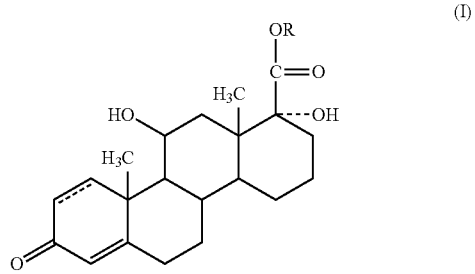

(I)

wherein R is H or $CH_3$ and the dotted line in ring A indicates that the 1,2-linkage is saturated or unsaturated, the amount of the compound of formula (I) being sufficient to enhance the anti-inflammatory activity or duration of action, or both, of loteprednol etabonate.

3. The method according to claim 1, wherein said composition is applied to the eyelid only.

4. The method according to claim 2, wherein said composition is applied to the eyelid only.

5. The method according to claim 2, wherein said composition comprises cortienic acid or $\Delta^1$-cortienic acid.

6. The method according to claim 2, wherein said composition comprises cortienic acid methyl ester or $\Delta^1$-cortienic acid methyl ester.

7. The method according to claim 2, wherein said composition comprises $\Delta^1$-cortienic acid.

8. The method according to claim 4, wherein said composition comprises cortienic acid or $\Delta^1$-cortienic acid.

9. The method according to claim 4, wherein said composition comprises cortienic acid methyl ester or $\Delta^1$-cortienic acid methyl ester.

10. The method according to claim 4, wherein said composition comprises $\Delta^1$-cortienic acid.

11. The method according to claim 1, wherein said composition is in the form of an ointment, a cream, a gel, a cream gel or a lotion.

12. The method according to claim 2, wherein said composition is in the form of an ointment, a cream, a gel, a cream gel or a lotion.

13. The method according to claim 3, wherein said composition is in the form of an ointment, a cream, a gel, a cream gel or a lotion.

14. The method according to claim 4, wherein said composition is in the form of an ointment, a cream, a gel, a cream gel or a lotion.

15. The method according to claim 1, wherein the dosage level of loteprednol etabonate is about 0.25% by weight of the composition.

16. The method according to claim 1, wherein the dosage level of loteprednol etabonate is about 0.50% by weight of the composition.

* * * * *